US 6,572,820 B2

(12) United States Patent
Onodera et al.

(10) Patent No.: US 6,572,820 B2
(45) Date of Patent: *Jun. 3, 2003

(54) STERILIZATION-PROTECTING AGENT AND STERILIZATION METHOD

(75) Inventors: Hirokazu Onodera, Oita (JP); Junsuke Suemitsu, Oita (JP)

(73) Assignee: Asahi Medical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,691

(22) PCT Filed: Feb. 4, 1997

(86) PCT No.: PCT/JP97/00269

§ 371 (c)(1),
(2), (4) Date: Aug. 4, 1998

(87) PCT Pub. No.: WO97/27878

PCT Pub. Date: Aug. 7, 1997

(65) Prior Publication Data

US 2002/0044884 A1 Apr. 18, 2002

(30) Foreign Application Priority Data

Feb. 5, 1996 (JP) ............................................. 8-040297

(51) Int. Cl.$^7$ ................................................. A61L 2/00
(52) U.S. Cl. .......................... 422/28; 204/157; 422/22; 422/40; 435/181
(58) Field of Search ................... 204/157, 28; 422/35, 422/20, 21, 22, 40; 435/69.8, 157, 173, 174, 175, 181

(56) References Cited

U.S. PATENT DOCUMENTS

| | | | | |
|---|---|---|---|---|
| 4,446,134 A | | 5/1984 | Naito et al. ................. | 424/101 |
| 4,620,908 A | * | 11/1986 | Van Duzer .................. | 204/157 |
| 4,876,241 A | | 10/1989 | Feldman et al. ............. | 424/101 |
| 5,217,881 A | * | 6/1993 | Park .......................... | 435/69.5 |
| 5,283,034 A | * | 2/1994 | Okrongly et al. ............. | 422/22 |
| 5,508,185 A | * | 4/1996 | Kawamura et al. ......... | 435/178 |

FOREIGN PATENT DOCUMENTS

| | | |
|---|---|---|
| EP | 0 267 015 | 5/1998 |
| JP | 56-83358 A | 7/1981 |
| JP | 4-218371 A | 8/1992 |
| JP | 04-285561 A | 10/1992 |
| JP | 07-328112 A | 12/1995 |
| WO | WO 89/06547 * | 1/1988 |
| WO | WO 89 06547 | 7/1989 |

* cited by examiner

Primary Examiner—Krisanne Thornton
(74) Attorney, Agent, or Firm—Dickstein, Shapiro, Morin & Oshinsky, LLP

(57) ABSTRACT

A material comprising a biologically active substance (or ligand) to be sterilized, including proteins (e.g., antibodies and enzymes), peptides, DNA, RNA, and glycoproteins, with or without a carrier, and sterilization-protecting agent comprising a trisaccharide or higher saccharide ("polysaccharide") having a positive charge, is provided. The skeletal background of the polysaccharide confers stability to the ligand and its positive charge traps destructive radicals produced during the sterilization process. The molecular weight ratio of sterilization-protecting agent to the ligand should be at least 1/500 but less than 1/2 to protect the ligand effectively without obstructing the ligand's activity. In particular, polysaccharides, such as chitosan (a polymer of D-glucosamine) and chitin which is partially converted into chitosan, are preferable as a sterilization-protecting agent. The biologically active substance in such a material is stabilized against various sterilization methods, including irradiation, wet heat, and chemical sterilization, either in a wet state or a dry state. Further, a method for sterilizing a biologically active substance in the presence of the above-described sterilization-protecting agent is provided.

28 Claims, No Drawings

STERILIZATION-PROTECTING AGENT AND STERILIZATION METHOD

TECHNICAL FIELD

The present invention relates to a material comprising a material to be sterilized and a sterilization-protecting agent comprising a trisaccharide or higher saccharide having a positive charge(s); a sterilization method using said sterilization-protecting agent; and said sterilization-protecting agent.

BACKGROUND ART

In recent years, attempts have been made on selective separation, division, removal, etc. of a substance interacting with a biologically active substance (hereinafter referred to simply as an active substance or a ligand), using said active substance; and research has been done on active materials obtained by immobilizing, as a biologically active substance, a ligand such as a peptide, protein, synthetic substance or the like onto a carrier. Investigations have been made particularly on techniques for specifically removing blood cells using an active material obtained by immobilizing a protein such as an enzyme, antibody or the like onto a carrier, or for using said active material as a bioreactor. These active materials, however, are very unstable to sterilization; particularly in the case of an active material having a ligand immobilized thereon, the interactivity of the ligand with a substance to be affected is reduced by sterilization in many cases and it has been difficult to conduct sufficient sterilization of the active material without impairing the activity of the ligand.

In U.S. Pat. No. 5,283,034, a sterilization method is disclosed which comprises conducting sterilization in the presence of a substance (e.g. human serum albumin) used as a surface stabilizer, and a mono- or di-saccharide (e.g. glucose, sucrose, lactose, trehalose or amylose) or a glycoprotein (e.g. immunoglobulin) used as an oxygen radical-capturing agent. In this sterilization method, however, sterilization is possible only in a dry state of less than 1% of water content; consequently, the sterilized material has an inferior priming property and has been difficult to handle.

In JP-A-4-285561, a sterilization method is disclosed which comprises sterilizing a medical appliance comprising a physiologically active protein as a main constituent, in the presence of a mono- or di-saccharide (e.g. sorbitol, mannitol, xylitol or trehalose). In this method, however, the target material to be sterilized is a substance (e.g. fibrin) which is water-insoluble and relatively stable to sterilization; therefore, when the to-be-sterilized material is a substance (e.g. an antibody) whose three-dimensional structure has a large effect on the expression of the activity, nothing was known for protecting the to-be-sterilized material.

Thus, no sterilization-protecting agent has been known sterilization of a ligand (e.g. a protein) having specificity, even in a wet state with the activity of the ligand being maintained.

DISCLOSURE OF THE INVENTION

In view of the above problems, the present invention has an object of providing such a sterilization-protecting agent that, a biological acting substance, can exhibit its function even after having been sterilized. The present invention also has an object of providing such a sterilization method that sterilization of a biological acting substance is possible even in a wet state with the activity of the substance being maintained.

The present inventors made an intensive study in order to solve the above problems. As a result, the present inventors have found that a sterilization-protecting agent comprising a polysaccharide, particularly a trisaccharide or higher saccharide having a positive charge(s) is very effective in sterilization. The present inventors further have found that when the above sterilization-protecting agent is used, a biological acting substance, even if it is a substance (e.g. an antibody) very unstable to sterilization, is surprisingly stable to sterilization in any state ranging from a wet state to a dry state. The finding has led to the completion of the present invention.

Hence, the present invention relates to a material comprising a material to be sterilized and a sterilization-protecting agent, wherein the sterilization-protecting agent comprises a trisaccharide or higher saccharide having a positive charge(s).

The present invention relates further to a sterilization method for material to be sterilized, which comprises sterilizing said material in the presence of a sterilization-protecting agent comprising a trisaccharide or higher saccharide having a positive charge(s).

The present invention relates furthermore to a sterilization-protecting agent comprising a compound containing a trisaccharide or higher saccharide having a positive charge(s).

BEST MODE FOR CARRYING OUT THE INVENTION

In the present invention, the sterilization-protecting agent refers to a material which can protect a material to be sterilized so that the material to be sterilized can, even after the sterilization, maintain its activity and exhibit its function. The present sterilization-protecting agent comprises a trisaccharide or higher saccharide having a positive charge(s).

In the sterilization-protecting agent of the present invention, it is thought that the positive charge(s) can quickly trap a radical generated during the sterilization, that the skeleton of trisaccharide or higher saccharide can increase the stability of a biological acting substance during the sterilization and can trap the above-mentioned radical although the effect is small, and that as a result, a high protection effect during sterilization can be obtained. It is also thought that direct bonding of a positive charge(s) to saccharide skeleton gives an even higher protection effect during the sterilization.

In the present invention, the trisaccharide or higher saccharide having a positive charge(s) refers to a homopolysaccharide wherein at least three monosaccharides of the same kind, each having a positive charge(s) is (are) bonded in series, or a heteropolysaccharide wherein at least three saccharides each having a positive charge(s) is (are) present and also other saccharide(s) is (are) present. Thus, the present polysaccharide must be composed of at least three monosaccharides each having a positive charge(s).

The constituent monosaccharides of the polysaccharide constituting the sterilization-protecting agent of the present invention, include for example, 3-amino-3-deoxy-D-ribose, D-galactosaminuronic acid, D-galactosamine, D-glucosaminuronic acid, D-glucosamine, D-gulosamine, D-talosamine, neosamine C, pneumosamine, D-fucosamine, D-mannosamine, mycaminose, mycosamine and rhodosamine. In the present invention, the polysaccharide is composed of at least three monosaccharides which are at least one of the above monosaccharides. The above monosaccharides (monomers) each have a positive charge(s)

owing to the amino group. The constituent monosaccharides of the polysaccharide may be those obtained by replacing the amino group of the above monosaccharide with an imino group.

The polysaccharide is preferably composed of at least three monosaccharides of which at least one monosaccharide is selected from the group consisting of D-galactosamine, D-glucosamine, D-gulosamine, D-talosamine, D-fucosamine, D-mannosamine, mycosamine and rhodosamine.

In the present invention, the polysaccharide is more preferably a chitosan, which is a polymer of D-glucosamine, and/or a chitin which is partially converted into chitosan. The chitosan which is a poly$\beta$1-4-glucosamine, is used most preferably because it has a positive charge(s) owing to the amino group. The chitin which is partially converted into chitosan is a saccharide partially having a poly$\beta$1-4-glucosamine structure as a result of deacetylation of chitin by hydrolysis or the like and must have at least three $\beta$1-4-glucosamine units. The chitin which is partially converted into chitosan is preferably water-soluble. The degree of conversion of chitin into a $\beta$1-4-glucosamine structure by hydrolysis or the like differs depending upon the molecular weight of chitin, but desirably is as high as possible in view of the water-solubility and the amount of a positive charge (s). The degree is preferably 20% or more, more preferably 50% or more, most preferably 80% or more.

The polysaccharide in the sterilization-protecting agent of the present invention desirably has a molecular weight which does not impair the function of ligand, biological acting substance, and which has an appropriate ratio to the molecular weight of ligand so that the ligand is not modified during sterilization. A ratio of the molecular weight of sterilization-protecting agent to the molecular weight of ligand, of ½ or more is not preferable because at such a ratio the interaction between ligand and biological to-be-affected substance (hereinafter referred to simply as to-be-affected substance, in some cases) is sterically impaired by the sterilization-protecting agent. Meanwhile, a ratio of the molecular weight of polysaccharide to the molecular weight of ligand, of less than 1/500 is not preferable because no sufficient protection effect during sterilization is obtained. Therefore, the molecular weight of the polysaccharide in the present invention is preferably 1/500 or more to less than ½ of the molecular weight of the ligand, more preferably 1/400 or more to less than ½ of the molecular weight of the ligand, most preferably 1/300 or more to less than ½ of the molecular weight of the ligand.

Particularly when a biomaterial (e.g. an anti-body) is used as the ligand, the polysaccharide is preferably a chitosan or a chitin which is partially converted to chitosan, each having a molecular weight of not less than 600 (trimer) and not higher than 100,000 (467-mer). From the standpoint of higher protectability during sterilization, the molecular weight of the polysaccharide is preferably close to the molecular weight of the ligand as long as the two molecular weights fall in the above conditions. The molecular weight of the sterilization-protecting agent is more preferably not less than 600 and not higher than 90,000 so that the sterilization-protecting agent does not impair the interaction between the ligand and the to-be-affected substance. The molecular weight of the sterilization-protecting agent is most preferably not less than 600 and not higher than 80,000.

The polysaccharide constituting the sterilization-protecting agent of the present invention may be an unmodified polysaccharide, or may be a terminal- or side chain-modified polysaccharide. The sterilization-protecting agent of the present invention may contain additives together with a polysaccharide. For the terminal or side chain modification, there can be used an appropriate structure which is relatively resistant to sterilization, such as alkyl chain, polyethylene glycol chain or the like. As the additives, any compounds can be used depending upon the application, and those having resistance to the sterilization are used preferably.

The sterilization-protecting agent of the present invention may be bonded to the ligand used as a to-be-sterilized substance or to the surface of a carrier for the ligand, or may be allowed to be present close to the ligand to stably protect the ligand during the sterilization. Allowing the sterilization-protecting agent to be present close to the ligand can be achieved by allowing the agent to be present in a diluent liquid in which a to-be-sterilized substance is placed for carrying out the sterilization of the substance. In order to achieve the co-existence of the sterilization-protecting agent of the present invention and a to-be-sterilized substance, the sterilization-protecting agent may be directly coated onto the to-be-sterilized substance.

In the present invention, "surface" refers to a surface with which a biological to-be-affected substance can come in contact. Therefore, the sterilization-protecting agent may be bonded to the surface of a carrier for biological acting substance (ligand).

The bonding of the sterilization-protecting agent to a ligand or to a substrate (e.g. porous material) as a carrier may be conducted in the form of direct covalent bond or covalent bond via an active group. In bonding the sterilization-protecting agent to a ligand or a carrier therefor such as a substrate (e.g. porous material), a substitution reaction, a condensation reaction, a ring-opening reaction or the like can be used. As the active group to be possessed by the surface of the carrier or by the ligand for bonding the sterilization-protecting agent thereto, there can be mentioned an active group formed by activation using a haloacetaminoalkylating agent; an epoxy group formed by activation using epichlorohydrin or the like; an active group formed by activation using an isocyanate group, an isothiacyanate group, an amino group, a carboxyl group, a hydroxyl group, a vinyl group or bromocyanogen; and so forth. As the active group formed by activation using a haloacetaminoalkylating agent, there can be mentioned an α-acetaminohalogen group formed by activation using an N-hydroxymethylhaloacetamide or the like; an α,β-propionaminohalogen group formed by activation using an N-hydroxymethyldihalopropionamide or the like; an α,α-acetaminodihalogen group formed by activation using an N-hydroxymethyldihaloacetamide or the like; an α,α,α-acetaminotrihalogen group formed by activation using an N-hydroxymethyltrihaloacetamide or the like; and so forth.

In the present invention, the polysaccharide does not include any substance wherein the saccharide chain and the a positive charge(s) are separated, such as glycoprotein.

In the present invention, the to-be-sterilized material may be any material to be sterilized, and there is no particular restriction thereto. The material is preferably a biological acting material comprising a biological acting substance showing an interaction with a biological to-be-affected substance and a carrier for the biological acting substance.

In the present invention, the biological acting substance (ligand) is a substance showing an interaction with a to-be-affected substance specifically or selectively, and is a substance having an affinity with the to-be-affected substance or a substance showing an action such as catalysis, activation, stimulation, reaction or the like on the to-be-affected substance. The kind of ligand used differs depending upon the to-be-affected substance used, but a protein and/or a peptide, or the like is generally used as the ligand.

As examples of the ligand having an affinity to those cells which are a hemocyte component of blood, particularly immunity-associated cells, a peptide having about 3 to 50 amino acid moieties is preferred in view of the low immunogenicity when dissolved inside a living body, and an antibody or the like is preferred in view of the high affinity with a to-be-affected substance. A monoclonal antibody is more preferred in view of the high affinity with cells. The antibody, when viewed from its function, can be exemplified by anti-CD4, anti-CD8, anti-CD3, anti-CD2, anti-CD1a, anti-CD1b, anti-CD5, anti-CD3R, anti-CD6, anti-CD7, anti-CD9, anti-CD10, anti-CD11a, anti-CD18, anti-CD19, anti-CD20, anti-CD21, anti-CD22, anti-CD23, anti-CD24, anti-CD37, anti-CD40, anti-CD72, anti-CD77, anti-CD16, anti-CD32, anti-CD33, anti-CD34, anti-CD35, anti-CD64, anti-CD65, anti-CDw65, anti-CD66b, anti-CD66e, anti-CD89, anti-CDw90, anti-CD56, anti-CD57, anti-CD94, anti-CD105, anti-CD106, anti-CD46, anti-CD31, anti-CD36, anti-CD41, anti-CD42a, anti-CD42b, anti-CD63, anti-CD11a, anti-CD11b, anti-CD11c, anti-CD18, anti-CD29, anti-CD44, anti-CD48, anti-CD49a, anti-CD49b, anti-CD49c, anti-CD49d, anti-CD49e, anti-CD49f, anti-CD50, anti-CD51, anti-CD54, anti-CD58, anti-CD61, anti-CD62E, anti-CD62L, anti-CD62P, anti-CD103, anti-CD26, anti-CD30, anti-CD69, anti-CD70, anti-CD71, anti-CD95, anti-CD25, anti-CD117, anti-CD122, anti-CDw124, anti-CD126 and anti-CD127. These antibodies may be used alone or in combinations of two or more. Further, even a peptide composed of part of such an antibody can be satisfactorily used as a ligand.

When the to-be-affected substance is a plasma component, the ligand showing an interaction with the substance includes all compounds or natural products, each having affinity with the plasma component. As examples of such a ligand, there can be mentioned antibodies to plasma component, such as anti-LDL antibody and the like; synthetic compounds having charges; polypeptides (oligopeptides) having not less than 3 and not higher than 50 amino acid moieties; high-molecular polymers.

The ligand, which shows a catalysis to a to-be-affected substance and has an action of selective reaction, selective modification or the like on the substance, can be found among compounds, natural products, substances contained in blood, etc. but is not restricted thereto. Preferred as such a ligand are proteins derived from an organism, such as mitogen, cytokine, enzyme and the like, in view of the requirement for high stability after sterilization. When the to-be-affected substance is a cell, the ligand also includes a cell-stimulating factor which can activate, inactivate, differentiate or propagate the cell or can show to the cell an immune response-controlling action, an anti-tumor action, an antiviral action or a cell propagation- or differentiation-controlling action.

Mitogen is also called a cell division-inducing substance and can not only induce cell division but also promote cell differentiation and impart a particular function to cells. Examples of mitogen include phytohemaglutinin (PHA), concanavalin A, kidney bean lectin (PHA), pork weed mitogen (PWM), lipopolysaccharide (LPS), streptolysin S, tuberculin protein (PPD), protein A and pneumococcal polysaccharide (SIII). In particular, pork weed mitogen (PWM) showing a strong activity to lymphocyte, lipopolysaccharide (LPS), etc. is used satisfactorily.

Cytokine is a proteinous factor which is released from cells and which mediates a cellular interaction, and is a substance which shows an immune response-controlling action, an anti-tumor action, an antiviral action or a cell propagation- or differentiation-controlling action. Examples thereof include interleukins 1 to 13; interferons $\alpha$, $\beta$ and $\gamma$; tumor necrosis factor; lymphotoxin; colony-stimulating factors such as granulocyte colony-stimulating factor (G-CSF), granulocyte macrophage colony-stimulating factor (GM-CSF) and the like; erythropoietin; epidermal growth factor; and fibroblast growth factor. In particular, a cytokine acting upon contact is satisfactory.

An enzyme is a catalyst produced by an organism and can exhibit a catalysis to a reaction, under mild conditions. The enzyme can be classified mainly into an oxidation-reduction enzyme, a transferase, a hydrolase, an excision and addition enzyme, an isomerase and a syntase. Any enzyme can be used satisfactorily.

In the present invention, the ligand may be bonded to a substrate (e.g. a porous material) which is a carrier for the ligand, or to a sterilization-protecting agent, in the form of a direct covalent bond or a covalent bond via an active group. In bonding the ligand to a carrier or a sterilization-protecting agent, any reaction can be used as long as the activity of the ligand is maintained, but a substitution reaction, a condensation reaction, a ring-opening reaction or the like is used preferably. As the active group, there can be used the same active group as used for bonding the sterilization-protecting agent of the present invention to a ligand, a carrier or the like; however, an active group formed using a haloacetaminoalkylating agent, an epoxy group or the like is used preferably, particularly from a reason that the ligand can be reacted therewith under mild conditions with the activity of the ligand being maintained. Particularly when the ligand is a biomaterial such as antibody or the like, an active group formed using a haloacetaminoalkylating agent is most preferred.

In the present invention, the carrier for ligand can be exemplified by a porous material, a film material, a plate-like material, a granular material and a tubular material. A porous material is preferred particularly. The porous material may be any shape as long as the porous material can have a contact with a to-be-affected substance. The shape preferably has a large surface area in order for the ligand to be able to contact with a to-be-affected substance in a liquid phase, at a high contact frequency. A preferable shape of the porous material includes fibrous structures such as fibrous, cotton-like, yarn-like, bundle-like, bamboo blind-like, woven fabric-like, nonwoven fabric-like and the like; polymeric porous materials such as sponge and the like; a bead shape; a gel shape; a hollow yarn shape; and so forth. Particularly when a cell component is separated, divided or removed from blood, a woven or nonwoven fabric is preferred for efficiency, and a nonwoven fabric is most preferred for easy control.

When the porous material has a nonwoven fabric shape, the average fiber diameter thereof can be selected appropriately. For example, when the to-be-affected substance is cells and the cells are specifically removed, a nonwoven fabric having an average fiber diameter of not less than 3 $\mu$m but less than 30 $\mu$m is used preferably. An average fiber diameter of less than 3 $\mu$m is not preferred because specific adsorption of components other than the to-be-affected substance increases. Meanwhile, an average fiber diameter of 30 μm or more is not preferred, because the contact frequency with the to-be-affected substance is significantly low and the efficiency is low. Therefore, when the to-be-affected substance is cells and the cells are specifically removed, the average fiber diameter is preferably not less than 3 μm but less than 25 μm, most preferably not less than 3 μm but less than 20 μm.

As the base material of the porous material, any material can be used satisfactorily as long as a sterilization-protecting agent or a ligand can be bonded thereto in the form of a covalent bond or a functional group can be introduced thereinto. As examples of the material which is preferable in view of the strength and practical applicability, there can be mentioned polyolefins such as polyethylene, polypropylene, polybutylene and the like; polystyrene derivatives such as polystyrene, polyalkylstyrenes, polyalkoxystyrenes, polyvinylnaphthalene and the like; polyaromatic-substituted ethylenes; polyesters such as polyethylene terephthalate and the like; polyvinyl alcohol type polymers; polymethacrylic acid esters such as polymethyl methacrylate, polybenzyl methacrylate and the like, and similar acrylate esters; polyamides such as nylon 66, nylon 6 and the like; copolymers or blends of a plurality of materials, such as polyethylene-polypropylene copolymer, styrene-butadiene copolymer, polypropylene-polystyrene blend and the like; and amorphous materials thereof. From the stability of the material and the easiness of functional group introduction, preferred as the material are polypropylene, polyethylene, polyethylene-polypropylene copolymer, etc., and more preferred are polypropylene, polyethylene-polypropylene copolymer.

In the present invention, the biological to-be-affected substance includes all substances that are affected by the above-mentioned ligand, but must have such a unique property as is specifically affected by the ligand. Examples of the to-be-affected substance include substances derived from an organism, particularly blood components or cells. Examples of the to-be-affected substance viewed from the kind of the ligand applied thereto are as follows. When the ligand is an antibody, there can be mentioned an antigen to the antibody, a cell having the antigen, or a plasma component acting as an antigen. When the ligand is a peptide having an affinity to an antigen, there can be mentioned the antigen, a cell having the antigen, or a plasma component acting as an antigen. When the ligand is an enzyme, a cytokine or a cell-stimulating factor, there can be mentioned a substrate to be affected by the enzyme or a cell to be affected to undergo activation, inactivation, differentiation, immune response or the like by the cell-stimulating factor or the cytokine.

In the present invention, as the blood components, there can be mentioned hemocyte components present in blood, such as lymphocyte, granulocyte, monocyte, platelet, hemopoietic stem cell and the like; plasma proteins such as albumin, γ globulin, basic protein, immunoglobulin, low-density lipoprotein, β2-microglobulin, retinol-bound protein, ceruloplasmin, transthyretin and the like; substances contained in plasma, such as bilirubin and the like; glycoproteins containing a saccharide in the structure; and so forth. However, the blood components are not restricted thereto. Biomaterials such as DNA, RNA and the like, and others are also included in the blood components. As particularly preferable examples of the blood components, there can be mentioned T cells such as helper T cell, suppressor T cell and the like; B cell; or hemopoietic stem cell.

In the present invention, the blood includes, besides ordinary blood, a lymphocyte suspension, a monocyte suspension, bone marrow fluid, cord blood, buffy coat, a platelet concentrate, an erythrocyte concentrate, a peripheral blood to which a hemopoietic factor such as G-CSF or the like is administered, etc. Further, it is possible to an anticoagulant, a blood preservative, etc. to these bloods, as needs arise.

In the present invention, the biological acting material (hereinafter referred to simply as the active material) is a to-be-sterilized material comprising a biological acting substance and a carrier. To sterilize the acting material, a known sterilization method is used such as irradiation sterilization, wet heat sterilization, chemical sterilization or the like. Preferably used is an irradiation sterilization which applies a radiation such as γ ray, electron beam or the like. The exposure of the radiation differs depending upon the density of the acting material and the viable count before sterilization, but is preferably at least 1 kGy. Irradiation of 80 kGy or more is not preferred because material other than ligand may be deteriorated. From the standpoint of the stability of sterilization effect, a more preferred exposure is not less than 2 kGy and not higher than 65 kGy and the most preferred exposure is not less than 2 kGy and not higher than 50 kGy.

In the present invention, it is preferred that the active material is sterilized in a wet state together with a diluting liquid in view of handling during use and the stability of the ligand during sterilization. The diluting liquid may be any liquid as long as it is a liquid which does not cause the deterioration of the ligand; however, the diluting liquid is preferably an aqueous solution which does not adversely affect the to-be-affected substance or the like even when the diluting liquid remains during use. When the to-be-affected substance is a blood component or the like, a liquid obtained by adding a sterilization-protecting agent to a salt-containing aqueous solution is used preferably. The pH of the diluting liquid is preferably not less than 4 but less than 12. A pH of less than 4 or 12 or more is not preferred because it tends to cause the deterioration of the ligand, etc. The pH of the diluting liquid is more preferably not less than 4 but less than 11, most preferably not less than 5 but less than 11.

When a sterilization-protecting agent is added to the diluting liquid, the concentration of the sterilization-protecting agent is selected appropriately. When an antibody is used as the ligand, the preferable concentration of the sterilization-protecting agent is not less than 0.1% by weight and not more than 15% by weight. A concentration of the sterilization-protecting agent of less than 0.1% by weight is not preferred because it is difficult to obtain a sufficient protecting effect during sterilization. Meanwhile, a concentration of the sterilization-protecting agent of more than 15% by weight is not preferred because it gives a high viscosity. The concentration of the sterilization-protecting agent is more preferably not less than 0.1% and not more than 10%, most preferably not less than 1% and not more than 10%.

The acting material according to the present invention is useful even when used in a nonaseptic state, but is particularly effective when used in an aseptic environment. In the present invention, the acting material can be used by being filled in a container having at least an inlet and an outlet, and can be used for specific removal or recovery of cells or for external circulation intended for specific removal of cells. The acting material can further be utilized for specific separation, adsorption, removal, etc. of cell fractions such as leukocyte, lymphocyte, monocyte, granulocyte and the like. The acting material can furthermore be used for specific removal and recovery of plasma component. When an enzyme or the like is used as the ligand, the acting material can be used for a bioreactor. When there is used, as the ligand, a material having a selective reactivity with and/or a selective modifiability for a to-be-affected substance, the acting material can be used for cell activation, etc.

Preferable examples of the application of the acting material according to the present invention are listed below.

1. A specific CD4 positive cell remover for removing only a particular hemocyte component in blood, wherein a porous material having an anti-CD4 monoclonal antibody as a ligand is filled in a container having an inlet and an outlet.

2. A specific CD34 separator for capturing and recovering only a particular hemocyte component in blood, wherein a porous material having an anti-CD34 monoclonal antibody as a ligand is filled in a container having an inlet and an outlet.

3. A specific CD3 cell remover for capturing and recovering only a particular hemocyte component in blood, wherein a porous material having an anti-CD3 monoclonal antibody as a ligand is filled in a container having an inlet and an outlet.

4. A specific LDL remover for capturing only a particular plasma component in blood, wherein a porous material having an anti-LDL monoclonal antibody as a ligand is filled in a container having an inlet and an outlet.

5. A specific CD4 positive cell remover for removing only a particular hemocyte component in blood, wherein a porous material having a peptide having an affinity with CD4 cell, as a ligand is filled in a container having an inlet and an outlet.

6. A specific LDL remover for capturing only a particular plasma component in blood, wherein a porous material having a peptide having an affinity with LDL, as a ligand is filled in a container having an inlet and an outlet.

7. A cell-stimulating device for stimulating only a particular cell component in blood, wherein a porous material having a mitogen as a ligand is filled in a container having an inlet and an outlet.

8. A cell-activating device for activating only a particular cell component in blood, wherein a porous material having a mitogen as a ligand is filled in a container having an inlet and an outlet.

9. A bioreactor for modifying only a particular substance in a solution, wherein a porous material having an enzyme as a ligand is filled in a container having an inlet and an outlet.

10. A cell-propagating device wherein a porous material having a cytokine as a ligand is filled in a container having an inlet and an outlet.

11. A cell incubator wherein a porous material having a cell-stimulating factor or a cell-propagating factor as a ligand is filled in a container having an inlet and an outlet.

12. A leukocyte-removing system for removing only a particular leukocyte component in blood, which contains a specific CD4 positive cell remover for removing only a particular blood corpuscle component in blood, in a blood circuit, in which remover a porous material having an anti-CD4 monoclonal antibody as a ligand is filled in a container having an inlet and an outlet.

The present invention is described in more detail below by way of the Examples, but is not restricted by the Examples.

EXAMPLE 1

2.15 g of N-hydroxymethylbromoacetamide and 100 ml of sulfolane were placed in a glass flask and stirred. Thereto was added 25 g of trifluoromethanesulfonic acid, followed by stirring. Therein was placed 0.1 g of a nonwoven fabric (average fiber diameter:4.5 μm) made of polystyrene, and a reaction was allowed to take place at 25° C. for 4 hours. After the reaction, the nonwoven fabric was taken out, washed with pure water and vacuum-dried to obtain an activated nonwoven fabric.

The nonwoven fabric was cut into circles having a diameter of 0.6 cm and immersed, at 4° C. for 2.5 hours, in 200 μL of an anti-human CD4 monoclonal antibody solution (hereinafter abbreviated to "anti-human CD4 solution") obtained by dissolving 72 μg of an anti-human CD4 monoclonal antibody ("Anti-CD4 Monoclonal Purified Antibody" of Immunotec Co.; molecular weight=55,000) in 500 μl of a phosphate buffer saline solution (hereinafter abbreviated to "PBS (−) solution") containing neither calcium nor magnesium, to immobilize the monoclonal antibody (hereinafter abbreviated to "antibody") on the nonwoven fabric. After the immobilization, the nonwoven fabric was washed with the PBS (−). Then, the nonwoven fabric was immersed in a PBS (−) solution containing 5% of chitosan (Wako Pure Chemical Industries, Ltd.; molecular weight =3,000 to 30,000 which is 1/50 to 1/5 of ligand molecular weight), to immobilize the chitosan at 4° C. for 2.5 hours. Thereafter, the nonwoven fabric was washed with the PBS (−) to obtain the intended acting material (filter).

Next, five sheets of the above filter were filled, together with the PBS (−) as a filling liquid, in a 1-ml container (a product of Movitech) having an inlet and an outlet, at a filling density of 0.1 g/cm$^3$, to prepare a column for CD4 positive cell separation. The column was irradiated with 25 kGy (exposure:1.5 kGy/h) of a γ ray by the use of a cobalt 60 irradiation equipment.

The resulting column was fed from the column inlet 3 ml of ACD-A-added human fresh blood (blood:ACD-A=8:1) at a rate of 1 ml/min using a syringe pump, and the treated blood was recovered from the column outlet.

The removal degree of CD4 positive cells was calculated by flow cytometry by measuring the numbers of CD4 positive cells in untreated blood and treated blood. The number of CD4 positive cells in untreated blood was $4.0 \times 10^5$ and that in treated blood was $4.0 \times 10^4$; therefore, the removal degree was 90%. In that case, the removal degree of CD8 positive cells, the removal degree of B lymphocytes and the removal degree of platelets were determined in the same manner; as a result, the removal degree of CD8 positive cells was 5%, the removal degree of B lymphocytes was 8%, and the removal degree of platelets was 20%. It was confirmed that CD4 positive cells could be removed specifically and that the activity of anti-CD4 antibody was maintained.

In order to confirm whether or not the column had been sufficiently sterilized by the above sterilization treatment, the viable count in filling liquid after sterilization was examined according to the procedure of the Pharmacopea of Japan. No microbe was detected in the diluting liquid after sterilization.

Comparative Example 1

The same experimental procedure as in Example 1 was conducted except that the 5% chitosan was replaced with a PBS (−) solution containing 5% of fructose which was a monosaccharide and had no positive charge (a product of Wako Pure Chemical Industries, Ltd. having a molecular weight of 180, which is 1/833 of ligand molecular weight). In this case, the removal degree of CD4 positive cells was 30%;

as to other cells, the removal degree of CD8 positive cells was 29% and the removal degree of B cells was 40%; the specific removability for CD4 positive cells, of the anti-CD4 monoclonal antibody-immobilized nonwoven fabric disappeared as a result of the γ ray irradiation.

EXAMPLE 2

2.15 g of N-hydroxymethyliodoacetamide, 50 ml of concentrated sulfuric acid and 40 ml of nitrobenzene were placed in a glass flask, and were made into a solution by stirring. Thereto was added 0.3 g of paraformaldehyde in an ice bath, followed by stirring. Thereinto was placed 0.1 g of a nonwoven fabric (average fiber diameter: 3.3 μm) made of a polypropylene, and a reaction was allowed to take place at 25° C. for 3 hours. After the reaction, the nonwoven fabric was taken out, washed with ethanol and pure water, and vacuum-dried to obtain an activated nonwoven fabric.

The nonwoven fabric was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−). Then, the nonwoven fabric was immersed in the same 5% chitosan PBS (−) solution as used in Example 1, to immobilize the chitosan at 4° C. for 2.5 hours. Thereafter, the nonwoven fabric was washed with the PBS (−) to obtain intended acting materials (filters).

In the same manner as in Example 1, ten of the above filters were placed, together with the 5% chitosan PBS (−) solution as a filling liquid, in a 1-ml container having an inlet and an outlet, at a filling density of 0.1 g/cm$^3$, to prepare a column. The column was irradiated with 35 kGy of a γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 81%. In that case, the removal degree of CD8 positive cells was 13%, the removal degree of B lymphocytes was 13%, and the removal degree of platelets was 25%. It was confirmed that CD4 positive cells could be removed specifically and that the activity of anti-CD4 antibody was maintained.

Comparative Example 2

The same experimental procedure as in Example 2 was conducted except that the 5% chitosan was replaced by a PBS (−) solution containing 5% of human albumin (glycoprotein) (a product of Beringer Manheim), used as an immobilizing solution and filling liquid. In that case, the removal degree of CD4 positive cells was 33%; the removal degree of CD8 positive cells was as high as 40%; the removal degree of B cells was as high as 29%; and specific removability of cells was not seen.

EXAMPLE 3

The same activated nonwoven fabric as used in Example 2 was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−).

In the same manner as in Example 1, five of the above filters and a PBS (−) solution containing 3% of glucosamine trimer (a product of Wako Pure Chemical Industries, Ltd.; molecular weight=611, which is 1/241 of ligand molecular weight) as a filling liquid were placed in a 1-ml container having an inlet and an outlet, at a filling density of 0.1 g/cm$^3$, to prepare a column. The column was irradiated with 25 kGy of a γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 83%. In that case, the removal degree of CD8 positive cells was 31%. It was confirmed that CD4 positive cells could be removed specifically and that the activity of anti-CD4 antibody was maintained.

EXAMPLE 4

The same activated nonwoven fabric as used in Example 2 was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−).

In the same manner as in Example 1, five of the above filters and a PBS (−) solution containing 7% of glucosamine pentamer (a product of Wako Pure Chemical Industries, Ltd.; molecular weight=1,006, which is 1/149 of ligand molecular weight) as a filling liquid were placed in a 1-ml container having an inlet and an outlet, at a filling density of 0.1 g/cm$^3$, to prepare a column. The column was irradiated with 25 kGy of a γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 79%. In that case, the removal degree of CD8 positive cells was 27%. It was confirmed that CD4 positive cells could be removed specifically and that the activity of anti-CD4 antibody was maintained.

EXAMPLE 5

The same activated nonwoven fabric as used in Example 2 was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−).

In the same manner as in Example 1, five of the above filters and a PBS (−) solution containing 5% of glucosamine heptamer (a product of Wako Pure Chemical Industries, Ltd.; molecular weight=1,401, which is 1/107 of ligand molecular weight) as a filling liquid were pladced in a 1-ml container having an inlet and an outlet, at a filling density of 0.1 g/cm$^3$, to prepare a column. The column was irradiated with 25 kGy of a γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 83%. In that case, the removal degree of CD8 positive cells was 27%. It was confirmed that CD4 positive cells could be removed specifically and that the activity of anti-CD4 antibody was maintained.

Comparative Example 3

The same activated nonwoven fabric as used in Example 2 was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−).

In the same manner as in Example 1, five of the above filters and a PBS (−) solution containing 5% of dextran sulfate, which is a polysaccharide having a negative charge (s) (a product of Sigma Co.; molecular weight=50,000, which is 1/3 of ligand molecular weight) as a filling liquid were placed in a 1-ml container having an inlet and an outlet, at a filling density of 0.1 g/cm$^3$, to prepare a column. The column was irradiated with 25 kGy of a γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 19%. In that case, the removal degree of CD8 positive cells was 22%. The specific removability for CD4 positive cells of the anti-CD4 monoclonal antibody-immobilized nonwoven fabric disappeared as a result of the γ ray irradiation.

Comparative Example 4

The same activated nonwoven fabric as used in Example 2 was cut into circles having a diameter of 0.68 cm and immersed in 200 μL of the anti-human CD4 solution dissolved in the PBS (−) (72 μg/500 μl), at 4° C. for 2.5 hours to immobilize the antibody on the nonwoven fabric. After the immobilization, the nonwoven fabric was washed with the PBS (−).

In the same manner as in Example 1, five of the above filters and a PBS (−) solution containing 3% of dextran sulfate, which is a polysaccharide having a negative charge (s) (a product of Sigma Co.; molecular weight=500,000, which is 1/0.3 of ligand molecular weight) as a filling liquid were placed in a 1-ml container having an inlet and an outlet, at a filling density of 0.1 g/cm$^3$, to prepare a column. The column was irradiated with 25 kGy of a γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 26%. In that case, the removal degree of CD8 positive cells was 22%. The specific removability for CD4 positive cells of the anti-CD4 monoclonal antibody-immobilized nonwoven fabric disappeared as a result of the γ ray irradiation.

Comparative Example 5

The same activated nonwoven fabric as used in Example 2 was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−).

In the same manner as in Example 1, five of the above filters and a PBS (−) solution containing 7% of heparin, which is a polysaccharide having a negative charge(s) (a product of The Green Cross Corporation; molecular weight= 17,000 to 20,000, which is 1/8 to 1/7.5 of ligand molecular weight) as a filling liquid were placed in a 1-ml container having an inlet and an outlet, at a filling density of 0.1 g/cm$^3$, to prepare a column. The column was irradiated with 25 kGy of a γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 16%. In that case, the removal degree of CD8 positive cells was 26%. The specific removability for CD4 positive cells of the anti-CD4 monoclonal antibody-immobilized nonwoven fabric disappeared as a result of the γ ray irradiation.

Comparative Example 6

The same activated nonwoven fabric as used in Example 2 was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−).

In the same manner as in Example 1, five of the above filters and a PBS (−) solution containing 5% of globulin (a glycoprotein) (a product of Beringer Manheim) as a filling liquid were placed in a 1-ml container having an inlet and an outlet, at a filling density of 0.1 g/cm$^3$, to prepare a column. The column was irradiated with 25 kGy of a γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 30%. In that case, the removal degree of CD8 positive cells was 26%. The specific removability for CD4 positive cells of the anti-CD4 monoclonal antibody-immobilized nonwoven fabric disappeared as a result of the γ ray irradiation.

Comparative Example 7

The same activated nonwoven fabric as used in Example 2 was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−).

Five of the above filters and a filling liquid, i.e. a PBS (−) solution containing 5% of human albumin, a protein (a product of Sigma Co.) and 5% of dextran, which is a polysaccharide having no positive charge (a product of Wako Pure Chemical Industries, Ltd.; molecular weight =10,000, which is 1/15 of ligand molecular weight) were placed in a 1-ml container having an inlet and an outlet, at a filling density of 0.1 g/cm$^3$, to prepare a column. The column was irradiated with 25 kGy of γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 28%. In that case, the removal degree of CD8 positive cells was 26%. The specific removability for CD4 positive cells of the anti-CD4 monoclonal antibody-immobilized nonwoven fabric disappeared as a result of the γ ray irradiation.

Comparative Example 8

The same activated nonwoven fabric as used in Example 2 was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−).

Five of the above filters and a filling liquid, i.e. a PBS (−) solution of a mouse monoclonal antibody, a protein (a product of Immunotec Co.) (72 μg/500 μl) were placed in a 1-ml container having an inlet and an outlet, at a filling density of 0.1 g/cm$^3$, to prepare a column. The column was irradiated with 25 kGy of γ ray.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 29%. In that case, the removal degree of CD8 positive cells was 29%. The specific removability for CD4 positive cells of the anti-CD4 monoclonal antibody-immobilized nonwoven fabric disappeared as a result of the γ ray irradiation.

Comparative Example 9

The same activated nonwoven fabric as used in Example 2 was cut into circles having a diameter of 0.68 cm and immersed in 200 μL of the anti-human CD4 solution (72 μg/500 μl) at 4° C. for 2.5 hours to immobilize the antibody on the nonwoven fabric. After the immobilization, the nonwoven fabric was washed with the PBS (−).

Five of the above filters and a filling liquid, i.e. a PBS (−) solution containing 5% of a glucosamine hydrochloride, which is a monosaccharide having a positive charge(s) (a product of Wako Pure Chemical Industries, Ltd.; molecular weight=216, which is 1/694 of ligand molecular weight) were placed in a 1-ml container having an inlet and an outlet, at a filling density of 0.1 g/cm$^3$, to prepare a column. The column was irradiated with 25 kGy of γ ray for sterilization.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 35%. In that case, the removal degree of CD8 positive cells was 24%. The specific removability for CD4 positive cells of the anti-CD4 monoclonal antibody-immobilized nonwoven fabric disappeared as a result of the γ ray irradiation.

EXAMPLE 6

The same activated nonwoven fabric as used in Example 2 was cut into circles having a diameter of 0.68 cm and immersed, at 4° C. for 2.5 hours, in 200 μL of the anti-human CD4 solution dissolved in the PBS (−) (72 μg/500 μl), to immobilize the antibody on the nonwoven fabric. After the immobilization, the nonwoven fabric was washed with the PBS (−).

Five of the above filters and a filling liquid, i.e. a PBS (−) solution containing 0.5% of galactosamine decamer (a product of Wako Pure Chemical Industries, Ltd.; molecular weight=1,621, which is 1/92 of ligand molecular weight) were placed in a 1-ml container having an inlet and an outlet, at a filling density of 0.1 g/cm$^3$, to prepare a column. The column was irradiated with 25 kGy of γ ray for sterilization.

In the same manner as in Example 1, 3 ml of an ACD-A-added human fresh blood (blood:ACD-A=8:1) was fed at a rate of 1 ml/min by the use of a syringe pump. The removal degree of CD4 positive cells was 81%. In that case, the removal degree of CD8 positive cells was 23%. It was confirmed that CD4 positive cells could be removed specifically and that the activity of anti-CD4 antibody was maintained.

EXAMPLE 7

2.15 g of N-hydroxymethyliodoacetamide, 50 ml of concentrated sulfuric acid and 40 ml of nitrobenzene were placed in a glass-made flask, and were made into a solution by stirring. Thereto was added 0.3 g of paraformaldehyde in an ice bath, followed by stirring. Thereinto was placed 0.1 g of a nonwoven fabric (average fiber diameter:3.3 μm) made of polypropylene, and a reaction was allowed to take place at 25° C. for 2 hours. After the reaction, the nonwoven fabric was taken out, washed with ethanol and pure water, and vacuum-dried to obtain an activated nonwoven fabric.

The nonwoven fabric was cut into circles having a diameter of 0.55 cm, and immersed, at 4° C. for 2.5 hours, in 100 μL of a solution of an alkaline phosphatase dissolved in the PBS (−) (0.0125 μg/μl), to immobilize the enzyme. After the immobilization, the nonwoven fabric was washed with the PBS (−). The nonwoven fabric was immersed in a PBS (−) solution containing 1% of chitosan (a product of Wako Pure Chemical Industries, Ltd.; molecular weight=3,000 to 30,000) to immobilize chitosan at 4° C. for 2.5 hours. Then, the nonwoven fabric was washed with the PBS (−) to obtain an intended acting material (a bioreactor).

The bioreactor was inserted into a 96-well microplate. The microplate was filled with a 1% chitosan solution as a filling liquid, and then irradiated with 5 kGy of γ ray.

After the sterilization, the filling liquid was replaced with the PBS (−) solution. Therein was placed 100 μL of a p-nitrophenylphosphoric acid-diethanolamine buffer solution (concentration=2 mg/ml). The resulting solution was allowed to stand at 25° C. for 5 minutes, and the nonwoven fabric was removed therefrom. Then, its absorbance at 405 nm was measured. The absorbance was 1.5 and it was confirmed that the activity of the enzyme was maintained. In that case, the absorbance of the control system in which only chitosan was immobilized was 0.1.

Comparative Example 10

The same Experimental procedure as used in Example 7 was conducted except that the 1% chitosan was replaced by a PBS (−) solution containing 1% of fructose, which is a monosaccharide having no positive charge (a product of Wako Pure Chemical Industries, Ltd.; molecular weight= 180, which is 1/833 of ligand molecular weight), to immobilize fructose to the nonwoven fabric, which was wet with the fructose solution. The absorbance after 5 minutes at 25° C. was 0.2 and the activity of the enzyme decreased apparently.

EXAMPLE 8

1 g of a chitin (a product of Wako Pure Chemical Industries, Ltd.; molecular weight=3,000 to 30,000, which is 1/50 to 1/5 of ligand molecular weight) was added to 100 ml of 5% sodium hydroxide and hydrolyzed at 50° C. for 5 hours to obtain chitin which had partially been converted into chitosan. This partially-converted-into-chitosan chitin was titrated with 1 N hydrochloric acid to measure its degree of conversion into chitosan, which was 70%.

The same experimental procedure as used in Example 7 was conducted except that a PBS (−) solution containing 1% of the above partially-converted-into-chitosan chitin was used as a sterilization-protecting agent in place of the 1% chitosan PBS (−) solution to immobilize the partially-converted-into-chitosan chitin to the nonwoven fabric, which was wet with the partially-converted-into-chitosan chitin solution and that the exposure of γ ray was changed to 25 kGy. The absorbance after 5 minutes at 25° C. was 0.9 and it was confirmed that the activity of the enzyme was maintained.

Comparative Example 11

The same experimental procedure as used in Example 8 was conducted except that the above PBS (−) solution containing 1% of a partially-converted-into-chitosan chitin was replaced by a PBS (−) solution containing 1% of dextran, which is a polysaccharide having no positive charge, to immobilize dextran to the nonwoven fabric, which was wet with the dextran solution. The absorbance after 5 minutes at 25° C. was 0.05 and the activity of the enzyme decreased.

EXAMPLE 9

2.15 g of N-hydroxymethyliodoacetamide, 50 ml of concentrated sulfuric acid and 40 ml of nitrobenzene were placed in a glass-made flask, and were made into a solution by stirring. Thereto was added 0.3 g of paraformaldehyde in an ice bath, followed by stirring. Thereinto was placed 0.1 g of a nonwoven fabric (average fiber diameter:3.3 μm) made of polypropylene, and a reaction was allowed to take place at 25° C. for 3 hours. After the reaction, the nonwoven fabric was taken out, washed with ethanol and pure water, and vacuum-dried to obtain an activated nonwoven fabric.

The nonwoven fabric was cut into circles having a diameter of 0.68 cm, and immersed in 200 μL of the anti-human CD4 solution (72 μg/500 μl) at 4° C. for 2.5 hours to immobilize the antibody. After the immobilization, the nonwoven fabric was washed with the PBS (−) solution. Then, the nonwoven fabric was immersed in the same 5% chitosan PBS (−) solution as used in Example 1, at 4° C. for 2.5 hours for coating. Thereafter, the resulting filter was refrigerated at −80° C. for 3 hours, followed by freeze-drying to obtain the intended acting materials (dry filters).

In the same manner as in Example 1, ten of the above dry filters were filled in a 1-ml container having an inlet and an outlet, at a placed density of 0.1 g/cm$^3$, to prepare a column. The column was irradiated with 15 kGy of γ ray.

The column was primed with 5 ml of the PBS (−) solution. Then, in the same manner as in Example 1, 3 ml of an ACD-A-added human fresh blood (blood:ACD-A=8:1) was fed at a rate of 1 ml/min by the use of a syringe pump. The degree of removal of CD4 positive cells was 80%. In that case, the degree of removal of CD8 positive cells was 12%. It was confirmed that CD4 positive cells could be removed specifically and that the activity of anti-CD4 antibody was maintained.

Industrial Applicability

By the use of the sterilization-protecting agent of the present invention, it is possible to sterilize a material containing a biological acting substance which has been impossible to sufficiently sterilize, and there is provided an acting material wherein a biological active substance can exhibit its function even after sterilization.

The acting material can be used for specific removal or recovery of cells or for external circulation intended for specific removal of cells. The acting material can be utilized for specific separation, adsorption, removal, etc. of cell fractions such as leukocyte, lymphocyte, monocyte, granulocyte and the like. The acting material can further be used for specific removal and recovery of plasma component. Also, when an enzyme or the like is used as the ligand, the acting material can be used as a bioreactor. Moreover, when there is used, as the ligand, a material having a selective reactivity with or a selective modifiability for a to-be-affected substance, the acting material can be used for cell activation, etc.

According to the present invention, there is further provided a sterilization method which enables sterilization of biological acting substance even in a wet state with the activity of the biological acting substance being maintained. According to this method, since a reactor in which a material having a biochemical acting substance is filled can be sterilized in a wet state, operations such as priming and the like can be conducted simply in using the reactor.

The present application claims a priority based on Japanese Patent Application No. 8-40297 filed on Feb. 5, 1996, the contents of which is incorporated herein in its entirety by reference.

What is claimed is:

1. A material comprising
   a to-be-sterilized material, and
   a sterilization-protecting agent comprising a trisaccharide or higher saccharide having a positive charge(s),
   wherein said to-be-sterilized material is a biological acting material comprising
   a biological acting substance immersed in an aqueous solution which interacts with a biological to-be-affected substance, and
   a carrier for said biological acting substance.

2. The material according to claim 1, wherein said carrier is a porous material and said biological acting substance is held on the surface of said porous material.

3. The material according to claim 1, wherein said trisaccharide or higher saccharide has a molecular weight which is at least 1/500 but less than ½ of the molecular weight of said biological acting substance.

4. The material according to claim 1, wherein said positive charge(s) of said trisaccharide or higher saccharide is owing to an amino group.

5. The material according to claim 1, wherein said trisaccharide or higher saccharide comprises a trisaccharide or higher saccharide of glucosamine and/or a derivative thereof.

6. The material according to claim 5, wherein said trisaccharide or higher saccharide is chitosan and/or chitin which is partially converted into chitosan.

7. A material comprising a to-be-sterilized material, and
   a sterilization-protecting agent comprising a trisaccharide or higher saccharide having a positive charge(s),
   wherein said to-be-sterilized material is a biological acting material comprising
   a biological acting substance immersed in an aqueous solution which interacts with a biological to-be-affected substance, and a porous material as a carrier for said biological acting substance, and
   said sterilization-protecting agent is bonded onto the surface of said porous material.

8. The material according to claim 1, wherein said biological acting substance is a protein and/or a peptide.

9. The material according to claim 8, wherein said biological acting substance is an antibody to a cell surface antigen and/or a peptide having an affinity to the cell surface antigen.

10. The material according to claim 9, wherein said antibody is a monoclonal antibody and/or a part thereof.

11. The material according to claim 9, wherein said cell is a blood cell.

12. The material according to claim 8, wherein said biological acting substance is any member selected from the group consisting of an enzyme, a cytokine and a cell-stimulating factor.

13. The material according to claim 2, wherein said porous material is a nonwoven fabric.

14. The material according to claim 1, wherein said biological to-be-affected substance is a blood component.

15. A sterilization method for a to-be-sterilized material, which comprises sterilizing said to-be-sterilized material in the presence of a sterilization-protecting agent comprising a trisaccharide or higher saccharide having a positive charge(s), wherein said to-be-sterilized material is a biological acting material comprising a biological acting substance immersed in an aqueous solution which interacts with a biological to-be-affected substance, and a carrier for said biological acting substance.

16. The method according to claim 15, wherein said sterilization is conducted in a state that said sterilization-protecting agent is bonded to said to-be-sterilized material.

17. The method according to claim 15, wherein said to-be-sterilized material is sterilized in a wet state.

18. The method according to claim 17, wherein said sterilization is conducted in a state where said sterilization-protecting agent is allowed to be present in a solution with which said to-be-sterilized material is in contact.

19. The method according to claim 18, wherein said sterilization is irradiation sterilization.

20. The method according to claim 19, wherein said irradiation sterilization is γ-ray sterilization.

21. The material according to claim 2, wherein said positive charge(s) of said trisaccharide or higher saccharide is owing to an amino group.

22. The material according to claim 3, wherein said positive charge(s) of said trisaccharide or higher saccharide is owing to an amino group.

23. The material according to claim 2, wherein said trisaccharide or higher saccharide comprises a trisaccharide or higher saccharide of glucosamine and/or a derivative thereof.

24. The material according to claim 3, wherein said trisaccharide or higher saccharide comprises a trisaccharide or higher saccharide of glucosamine and/or a derivative thereof.

25. The material according to claim 4, wherein said trisaccharide or higher saccharide comprises a trisaccharide or higher saccharide of glucosamine and/or a derivative thereof.

26. The material according to claim 23, wherein said trisaccharide or higher saccharide is chitosan and/or chitin which is partially converted into chitosan.

27. The material according to claim 24, wherein said trisaccharide or higher saccharide is chitosan and/or chitin which is partially converted into chitosan.

28. The material according to claim 25, wherein said trisaccharide or higher saccharides is chitosan and/or chitin which is partially converted into chitosan.

\* \* \* \* \*